(12) United States Patent
Massia et al.

(10) Patent No.: US 6,586,493 B1
(45) Date of Patent: Jul. 1, 2003

(54) POLYSACCHARIDE-BASED HYDROGELS AND PRE-GEL BLENDS FOR THE SAME

(75) Inventors: Stephen P. Massia, Apache Junction, AZ (US); Julie Trudel, Sunnyvale, CA (US)

(73) Assignee: Arizona Board of Regents Arizona State University, Tempe, AZ (US)

( * ) Notice: Subject to any disclaimer, the term of this patent is extended or adjusted under 35 U.S.C. 154(b) by 23 days.

(21) Appl. No.: 09/801,373

(22) Filed: Mar. 7, 2001

(51) Int. Cl.[7] .............................. C08F 2/46; C08L 5/00; C08L 5/02
(52) U.S. Cl. ........................... 522/87; 522/88; 522/89; 522/42; 522/44; 523/105; 523/109; 523/111; 523/112; 523/113; 527/200; 527/201; 527/300; 527/314; 424/488
(58) Field of Search .............................. 522/84, 44, 87, 522/88, 89, 42; 523/105, 109, 111, 112, 113; 527/300, 200, 201, 202, 314

(56) References Cited

U.S. PATENT DOCUMENTS

| | | | |
|---|---|---|---|
| 4,957,744 A | | 9/1990 | della Valle et al. |
| 5,192,326 A | * | 3/1993 | Bao et al. ................ 623/17.12 |
| 5,346,935 A | * | 9/1994 | Suzuki et al. ................ 424/486 |
| 5,410,016 A | * | 4/1995 | Hubbell et al. ............. 128/898 |
| 5,648,592 A | * | 7/1997 | Pierce ......................... 110/342 |
| 5,677,276 A | | 10/1997 | Dickerson et al. |
| 5,763,504 A | | 6/1998 | Matsuda et al. |
| 5,834,556 A | * | 11/1998 | Desai et al. |
| 5,836,970 A | | 11/1998 | Pandit |
| 5,900,245 A | * | 5/1999 | Sawhney et al. ........... 128/898 |

OTHER PUBLICATIONS

M.S. Agren, "An Amorphous Hydrogel Enhances Epithelialisation of Wounds," Acta Derm Venereol (Stockh), 78:119–122 (1998).

Boswell et al., "Denucleation Promotes Neovascularization of ePTFE in vivo," J. Biomater. Sci. Polymer Edn., 10(3):319–329 (1999).

Van der Lei et al., "Enhanced Healing of 30 μm Gore–Tex PTFE Microarterial Prostheses By Alcohol–Pretreatment," British Journal of Plastic Surgery, 44:428–433 (1991).

Marler et al., "Soft–Tissue Augmentation With Injectable Alginate and Syngeneic Fibroblasts," Plastic and Reconstructive Surgery, 105(6):2049–2058 (May 2000).

Sawhney et al., "Bioerodible Hydrogels Based on Photopolymerized Poly(ethylene glycol)–co–poly(α–hydroxy acid) Diacrylate Macromers," Macromolecules, 26:581–587 (1993).

Turner et al., "Self–Association of Hyaluronate Segments in Aqueous NaCl Solution," Archives of Biochemistry and Biophysics, 256(2):484–495 (Sep. 1988).

Van Dijk–Wolthuis et al., "Synthesis, Characterization, and Polymerization of Glycidyl Methacrylate Derivatized Dextran," Macromolecules, 28:6317–6322 (1995).

West et al., "Angiogenesis Induced by Degradation Products of Hyaluronic Acid," Science, 228:1324–1326 (Jun. 1985).

* cited by examiner

Primary Examiner—Susan W. Berman
(74) Attorney, Agent, or Firm—Pitney, Hardin, Kipp & Szuch, LLP

(57) ABSTRACT

Disclosed are hyaluronate-containing hydrogels having angiogenic and vascularizing activity and pre-gel blends for preparing the hydrogels. The hydrogels contain a cross-linked matrix of a non-angiogenic hyaluronate and a derivatized polysaccharide material, in which cross-linking is effected by free-radical polymerization. Kits for preparing the hydrogels are also disclosed.

14 Claims, 3 Drawing Sheets

POLYSACCHARIDE-BASED HYDROGELS AND PRE-GEL BLENDS FOR THE SAME

Financial assistance for this work was provided by the United States Government under National Institutes of Health Grant Number HL 6045004GR. Accordingly, the United States Government may own certain rights to invention.

FIELD OF THE INVENTION

The present invention relates polymeric hydrogel blends, and more particularly to polymeric hydrogel blends that exhibit angiogenic and vascularizing activity.

BACKGROUND OF THE INVENTION

Hydrogels are usually formed by chemical and physical cross-linking reaction between molecules using for example light energy and light-activated free radical initiators to promote chemical cross-linking (U.S. Pat. No. 4,957,744 to della Valle). Photo cross-linkable polymers are typically chemically modified (activated) to provide reactive groups for the crosslinking reaction. Successful examples include photocurable hydrogels made from synthetic materials, such as polyethylene glycol (Sawhney, et al., Bioerodible Hydrogels Based On Photopolymerized Poly(Ethylene Glycol)-Co-Poly(A-Hydroxy Acid) Diacrylate Macromers, Macromolecules, 26(4):581–587 (1993)), and also from macromolecules of biological origin. Hydrogels made of derivatized polysaccharides are formed using such a procedure (U.S. Pat. No. 5,763,504 to Takehisa Matsuda, et al.).

In the field of medical research, hydrogels are used to provide scaffolds to support cell growth in tissue replacement and regeneration applications, or to serve as drug delivery vehicles by adding drugs to the hydrogel. The drug may either be entrapped in the gel, or the molecules can be ionically or covalently bound to the backbone of the hydrogel (U.S. Pat. No. 5,677,276 to Dickerson, et al.). Hydrogels can also be implanted without the addition of cells or drugs, and serve some space filling cosmetic or anatomical purposes, such as tissue augmentation (Marler, et al., Soft-Tissue Augmentation With Injectable Alginate And Syngeneic Fibroblasts, Plast Reconstr Surg, 105(6):2049–58 (2000)). Bioactive hydrogels intrinsically elicit a specific host response, such as promoting the migration of certain cells or tissue ingrowth (Agren, M S., An Amorphous Hydrogel Enhances Epithelialisation Of Wounds, Acta Derm Venereol, 78(2):119–22 (1998)).

Host reactions of interest, angiogenesis and neovascularization, entail the formation of new blood vessels sprouting from the vascular bed surrounding the hydrogel implant and their growth into the hydrogel implant, respectively. Several angiogenic substances have been identified, including small fragments of the tissue matrix polysaccharide hyaluronate, ranging between 4 and 25 disaccharides in length (D C West, et al., Angiogenesis Induced By Degradation Products Of Hyaluronic Acid, Science, 228(4705):1324–6 (1985)). Hyaluronate, a tissue extracellular matrix glycosaminoglycan of approximately 1 million Daltons molecular weight, is naturally broken down into smaller fragments by the action of an enzyme, hyaluronidase, or by hydrolysis. Fractionation of hyaluronate may be accomplished in vitro using the enzyme hyaluronidase (Turner, et al., Self-Association Of Hyaluronate Segments In Aqueous NaCl Solution, Arch. Biochem. Biophys., 265(2):484–95 (1988)). However, to isolate the desired fragment size, time and manipulation are required.

In view of the art, there is a need for angiogenic hyaluronate-containing hydrogels that avoids the time-consuming and costly fractionation methods associated with the production of small hyaluronate fragments. Accordingly, it is an object to provide angiogenic hyaluronate-containing hydrogels that avoids these time-consuming and costly production methods.

SUMMARY OF THE INVENTION

The present invention provides hydrogels having angiogenic activity and pre-gel blends for synthesizing the hydrogels. The pre-gel blend includes a mixture of a polysaccharide material at least partially substituted with an unsaturated, cross-linking moiety, and a non-angiogenic hyaluronic acid or salt thereof. Preferably, the polysaccharide material has an average molecular weight of at least about 10,000 Daltons, with at least about 40,000 Daltons being more preferred. Classes of polysaccharide material to be used are starch or starch derivatives, water-soluble gums, or mixtures thereof. Examples of starch or starch derivatives are dextrans, curdlans, succinoglycans, pullulans, cellulose derivatives, cyclodextrins, or mixtures thereof Examples of water-soluble gum are alginates, carageenens, xanthans, galactomannans, or mixtures thereof. In a particular embodiment, the starch or starch derivative is dextran. Preferably, the unsaturated, cross-linking moiety is selected from the group consisting of acrylates, esters, ethers, thioethers, amides, enamides, sulfonyl esters or mixtures thereof, with acrylate being particularly preferred. The non-angiogenic hyaluronic acid or salt preferably has an average molecular weight of at least about 500,000 Daltons, with at least about 1,000,000 Daltons being more preferable.

The hydrogels of the present invention are a reaction product prepared by a process which includes: admixing the polysaccharide material that is at least partially substituted with the unsaturated, cross-linking moiety, and the non-angiogenic hyaluronic acid or salt thereof, with a free-radical initiator in a solvent; and cross-linking the mixture to form the hydrogel. The free-radical initiator is either a chemical initiator and a non-chemical initiator, with a non-chemical initiator (e.g., UV initiator) being preferred. A preferred class of UV initiators are acetophenone derivatives. The solvent is preferably water, a water-based solvent, a water-miscible organic solvent, or mixtures thereof. The other components are as described above.

The present invention also provides kits for preparing the hydrogels. In one embodiment the kit includes: a first container containing a mixture of the partially substituted, polysaccharide material and the non-angiogenic hyaluronic acid or salt thereof; and a second container containing a free-radical initiator. In another embodiment the kit includes: a first container containing the partially substituted, polysaccharide material; a second container containing the non-angiogenic hyaluronic acid or salt thereof; and a third container containing the free-radical initiator. Preferably, the kits further include an instruction pamphlet for preparing the hydrogel.

Advantageously, the pre-gel blends and hydrogels of the present invention omit the use of angiogenic hyaluronate fragments as a starting material while providing angiogenic hyaluronate-containing hydrogels. These and other advantages of the invention will become more readily apparent from the detailed description set forth below.

DETAILED DESCRIPTION OF THE INVENTION

Figure 1:
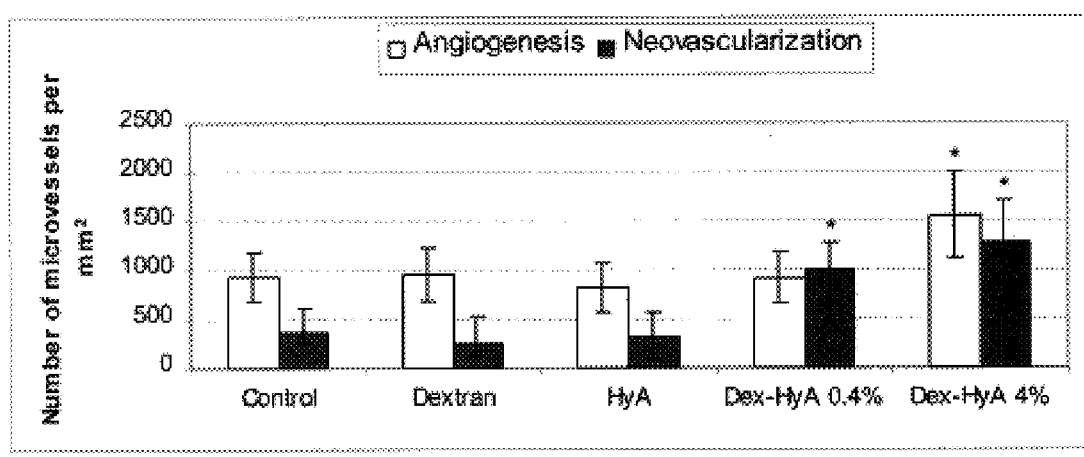
FIG. 1 is a bar graph illustrating microvessel distribution (angiogenesis and neovascularization) at the abluminal interface of impregnated ePTFE disks implanted in the adipose tissue of rats.

The present invention provides hydrogels having angiogenic activity and pre-gel blends for synthesizing the hydrogels. The hydrogels of the invention advantageously avoid the use of small hyaluronate fragments while at the same time providing angiogenic and vascularizing activity.

The pre-gel blend of the invention includes a mixture of a polysaccharide material at least partially substituted with an unsaturated, cross-linking moiety, and a non-angiogenic hyaluronic acid or a salt thereof. In accordance with the present invention, the polysaccharide material is any polysaccharide material with a polysaccharide material other than hyaluronic acid or its salt being preferred. In another embodiment, the polysaccharide material is preferably a water-soluble polysaccharide. Two preferred classes of polysaccharides to be used are starch or starch derivatives and water-soluble gums. Representative examples of starch or starch derivatives to be used include, but are not limited to, dextrans, curdlans, succinoglycans, pullulans, cellulose derivatives, cyclodextrins and mixtures thereof. One particularly preferred starch derivative to be used is dextran. Representative examples of water-soluble gums to be used include, but are not limited to, alginates, carrageenans, xanthans, galactomannans and mixtures thereof.

In accordance with the invention, the polysaccharide material can have varying molecular weights. In a preferred embodiment a polysaccharide material with an average molecular weight of at least about 10,000 Daltons is used, with at least about 40,000 Daltons being more preferred. Likewise, the polysaccharide material should preferably have an average molecular weight less than about 2,000,000 Daltons for ease of preparation. Polysaccharide materials with higher molecular weights can be used however decreased water solubility becomes a factor.

The polysaccharide material has at least a portion of its substituents derivatized with an unsaturated, cross-linking moiety. The cross-linking moiety is derived from any heterofunctional cross-linking agent that can bonded to the saccharide residues while providing at least one vinyl group to effect cross-linking via free-radical polymerization. The polysaccharide material is substituted with the unsaturated, cross-linking moiety using any technique known in the art. As will apparent to the skilled artisan, the specific technique utilized will depend on the functional groups available on the saccharide residues and the cross-linking agent. In most instances, the saccharide residue will have free hydroxyl groups that provide available sites for attachment of the cross-linking agent. In a preferred embodiment, the cross-linking moiety is non-photoreactive and contains a hydrophilic functional group. "Non-photoreactive" means that the cross-linking moiety is substantially light insensitive (i.e., does not undergo free-radical polymerization without a free-radical initiator). Examples of functional groups in which available hydroxyl groups of the polysaccharide material can be derivatized to include, but are not limited to, acrylates, esters, ethers, thioethers, amides, enamides, sulfonyl esters and mixtures thereof.

In a particularly preferred embodiment, the unsaturated cross-linking moiety is an acrylate (i.e., an acryloyl) group.

An example of a cross-linking agent to be used to derivatize the polysaccharide material is a glycidyl acrylate such as glycidyl methacrylate. Other cross-linking agents to be used are epichlorohydrin, borate, glyoxal, and glutaraldehyde. The derivatization of free-hydroxyl groups of a polysaccharide materials is achieved following conventional techniques known in the art. One technique is described in van Dijk-Wolthuis, et al., Synthesis, Characterization, and Polymerization of Glycidyl Methacrylate Derivatized Dextran. Macromolecules, 28:6317–6322 (1995), which is incorporated herein by reference. Following synthesis, the derivatized polysaccharide material can be lyophilized (i.e., freeze-dried) for storage.

In accordance with the invention, the polysaccharide material is partially derivatized with the unsaturated cross-linking moiety. The level of derivatization is variable and is dependent on the desired physical properties (e.g., viscosity) for the hydrogel end product. In a preferred embodiment, the polysaccharide material has a degree of substitution (DS) of at least about 4, with about 7 being more preferred and about 15 being even more preferred. If desired, DS levels of 22, 35 or greater can also be utilized. As will be apparent to those skilled in the art, degree of substitution refers to the molar ratio of cross-linking moiety per saccharide residue. The advantage of greater DS levels is reduced gelation time. The DS level of the derivatized material can be ascertained following conventional techniques, such a Nuclear Magnetic Resonance (NMR). These and other parameters can be easily ascertained by those skilled in the art following the teachings of the invention.

As previously described, the second component for the pre-gel blends and hydrogels of the invention is a non-angiogenic hyaluronic acid or salt thereof (i.e., a hyaluronate). In the context of the invention, a non-angiogenic hyaluronate is a hyaluronate that contains greater than 25 disaccharide units which corresponds to an average molecular weight of greater than 10,000 Daltons. As known from the prior art, hyaluronate fragments greater than 25 disaccharide units do not exhibit angiogenic activity. In a preferred embodiment, the hyaluronate has an average molecular weight of at least about 500,000 Daltons, with an average molecular weight of at least about 1,000,000 Daltons being preferred. A particular advantage of the invention is that unfractionated (i.e., native) hyaluronates are used as a starting material rather than fractionated hyaluronate fragments, which significantly reduces costs and time constraints for producing angiogenic hyaluronate-containing hydrogels.

To form the hydrogel, the derivatized polysaccharide material and the hyaluronate are mixed in the presence of a suitable solvent. Suitable solvents to be used are water or water-based solvents, water-miscible organic solvents, or combinations thereof. Example of water-miscible organic solvents include, but are not limited to, methanol, ethanol, acetone, dioxane, dimethylformamide, and tetrahydrofuran. In a preferred embodiment water or a water-based solvent (e.g., buffered saline) is used to induce sufficient swelling of the polysaccharide material to provide a viscous solution (a hydrogel precursor). The desired viscosity of the solution and resulting hydrogel end product is variable and can be tailored for the particular end use for contemplated for the hydrogel. For example, to impregnate an arterial prostheses, a relatively low viscosity solution is preferable for ease of use.

The hyaluronate and the derivatized polysaccharide material are mixed using any conventional technique known in the art. The ratio of hyaluronate to derivatized polysaccharide material is any ratio that exhibits increased angiogenesis or vascularization over either component alone. Preferably, the resulting mixture of the two components contains at least about 0.1 percent by weight of hyaluronate, with at least about 0.4 weight percent being more preferred, and about 4 weight percent being even more preferred. Greater concentrations of hyaluronate can also be used but may require increased preparation times due to increasing solution viscosities.

Cross-linking of the mixture is effected by the addition of a free-radical polymerization initiator to the solution to induce cross-linking via the vinyl groups of the cross-linking moieties. Examples of free radical initiators are well-known in the art with a description of free-radical initiators being found in Kirk-Othmer, Encyclopedia of Chemical Technology, 14:431–460 (1995), which is incorporated herein by reference. In accordance with the invention, any free-radical initiator is used to effect cross-linking. In a preferred embodiment, non-chemical initiators are used to allow for subsequent handling of the mixture before cross-linking. Chemical initiators (e.g., peroxide initiators) are used if handling of the mixture after addition of the initiator is not required or limited. One particularly preferred class of non-chemical initiators are photoinitiators (i.e., UV-initiators) such as acetophenone derivatives. An example of an acetophenone derivative is 2,2-dimethoxy-2-phenylacetophenone.

In another embodiment, the present invention provides a kit for preparing a hydrogel having angiogenic and vascularizing activity. The kit includes a first container which contains the pre-gel blend and a second container which contains the free-radical polymerization initiator. In accordance with the invention, the first and second containers can also be the first and second compartments of a single container structure. The kit can also include an instruction pamphlet providing instructions on using the kit to synthesize the hydrogel. In an alternative embodiment the kit includes a first container which contains the derivatized polysaccharide material, a second container which contains the non-angiogenic hyaluronic acid or salt thereof, and a third container which contains the free-radical polymerization initiator.

The hydrogels of the present invention due to their angiogenic and vascularizing activity are useful for a variety of medical applications. In particular, the hydrogels are particularly suitable for wound healing applications such as wound dressings and porous prostheses.

The following non-limiting examples illustrate the synthesis of the pre-gels and hydrogels of the present invention and their angiogenic and vascularization properties.

EXAMPLES

Example 1

Dextran molecules were derivatized with methacryloyl functional groups according to procedure detailed in van Dijk-Wolthuis, et al., Synthesis, Characterization, and Polymerization of Glycidyl Methacrylate Derivatized Dextran, Macromolecules, 28:6317–6322 (1995). Dextran-tetramethylrhodamine (dex-rhod) (Av. Mol. Wt.: 40,000, Molecular Probes) and dextran (dex) (Av. Mol. Wt.: 40,000, Sigma Chemical Co.) were mixed in a 0.04% (w/w) ratio (dex-rhod/dex). This mixture was chemically modified by dissolving the mixture and a catalyst, dimethylaminopyridinine (DMAP) (Sigma Chemical Co.), in dimethylsulfoxide (DMSO) (Mallinckrodt Baker Inc.) under nitrogen atmosphere at room temperature. Glycidyl methacrylate (GMA) (Sigma Chemical Co.) was then added to the mixture to produce derivatized dextran (acryloyl-dex). The amount of GMA was calculated to obtain a degree of substitution (DS: molar ratio of GMA per glucopyranose residue) equal to 15. After 48 hours of stirring, an equimolar amount of hydrochloric acid (HCl) was added to the chemical reaction to neutralize the action of the catalyst.

Acryloyl-dex and DMSO were then separated using dialysis sacks having a molecular weight cutoff of 12,000 (Sigma Diagnostic Inc.), and also using DMSO-resistant centrifugal filter devices (Centricon Plus-20, Millipore corporation) with a swing-bucket centrifuge set at 4000 rpm and 40° C. The filtrate (acryloyl-dex) was then collected and dissolved in deionized water. The solutions were frozen and lyophilized for a few days. The product was then stored frozen in its powdered form.

A few milligrams of the lyophilized acryloyl-dex were dissolved in deuterium oxide (Aldrich Chemical Company Inc.), in NMR tubes. The materials were characterized using proton nuclear magnetic resonance (Gemini 300 MHz spectrometer, Varian Associates Inc, Palo Alto). This allowed for confirming that the acryloylation reaction took place, and also allowed for calculating the empirical degree of substitution of the acryloylated polysaccharides. For comparison purposes, $^1$H-NMR spectra were also acquired for unmodified dextran. The $^1$H-NMR spectrum for acryloyl-dex presented the typical characteristics of chemically modified dextran backbone through the addition of GMA. The anomeric proton from the glucopyranosal ring ($\alpha$1,6) was clearly seen at ~$\delta$ 5.0 ppm. The proton seen at $\delta$ 5.3 ppm was from the anomeric carbon due to $\alpha$ 1,3 linkages. Signals from the methacryloyl group were seen at $\delta$ 1.95 ppm for the methyl protons and at $\delta$ 5.75 and $\delta$ 6.2 ppm for the protons at the double bond. From the integral values, the experimental DS of acryloyl-dex was calculated as first detailed by van Dijk-Wolthius et al. The acryloyl-dex was determined to have an empirical degree of substitutions of 18.

Example 2

A comparative hydrogel was prepared using the acryloyl-dex prepared in Example 1. Briefly, acryloyl-dex was dissolved in Dulbecco's phosphate-buffered saline (PBS) (Life Technologies, Inc.) to form a 25% weight/volume (w/v) solution. Free radical polymerization was accomplished by adding photoinitiators to the solution, after which the solution was syringe filtered. The photoinitiators consisted of a 30% solution of solid 2,2-dimethoxy-2-phenylacetophenone (Aldrich Chemical Company Inc.) mixed into 1-vinyl-2-pyrrolidinone (Aldrich Chemical Company Inc.). Three microliters of photoinitiators were added for each milliliter of solution (hydrogel precursor designated "Dextran"). The solution was exposed to long-wave ultraviolet radiation (Black-Ray, UVP Inc.; radiation range of 315–400 nm, peak at 365 nm) which lasted up to 5 minutes, until a hydrogel was formed.

Example 3

A comparative hyaluronate solution was prepared. Hyaluronate (sodium salt) (HyA, Av. Mol. Wt.: 2,000,000, Kyowa Hakko Kogyo Co., Ltd.) was dissolved in PBS to form a 1% (w/v) viscous mixture and a trace amount of 5-(and-6-)-carboxytetramethyl-rhodamine (rhod) (av. Mol. Wt.: 430.46, Molecular Probes) was incorporated into the viscous solution (designated "HyA").

Example 4

Two inventive hydrogels were prepared by first dissolving the powdered acryloyl-dex of Example 1 in PBS to form a 25% (w/v) solution. Photoinitiator mixtures as described in Example 2 were added to the solutions. The solutions were filtered following the procedure of Example 2. Sterile powdered hyaluronate (2,000,000 Daltons average molecular weight) was added to the filtered solutions (weight/volume percentages of HyA/acryloyl-dex of 0.4% and 4%), and thoroughly mixed. The viscous solutions (hydrogel precursors designated "Dex-HyA") were exposed to long-wave ultraviolet radiation for five minutes to induce cross-linking as in Example 2.

Example 5

The angiogenic and vascularizing properties of the hydrogels were evaluated using a rodent model. The materials were evaluated using a hybrid system where the gels are impregnated into the interstices of expanded polytetrafluoroethylene (ePTFE). ePTFE vascular grafts (80-cm-long, 6-mm inside diameter, 20 µm internodal distance, wall thickness of approximately 400 µm) were cut into 10 cm-long segments under a laminar flow hood. Denucleation of the graft is performed using the procedure described in Van der Lei, et al., Enhanced healing of 30 microns Gore-Tex PTFE microarterial prostheses by alcohol-pretreatment, Br. J. Plast. Surg., 44(6):428–33 (1991), in which ten alcohol baths were utilized to remove trapped air from the void space of the grafts and followed by two baths using PBS containing 1000 mg/L D-glucose, 36 mg/L of sodium pyruvate, calcium and magnesium (Life Technologies, Inc.). The graft segments were allowed to dry under the laminar flow hood for 24 hours. A set of these segments served as a control.

Graft segments were impregnated with the hydrogel precursors of Example 2–4 using a sterile syringe containing the sterile solution. The viscous solution was forced through the graft interstices. A knot was tied in the distal end of the graft segment. The proximal end was tightly wrapped around the syringe, using a three-way connecting luer-port. The viscous solution was infused into the void space of the graft by applying pressure with the syringe plunger for several seconds. A well was placed directly underneath the graft to collect any excess gel precursor seeping through the graft. The graft specimen was detached, and 6 mm-diameter ePTFE disks were punched out of impregnated segments of vascular grafts, using an autoclaved biopsy punch. Cross-linking of the hydrogel precursor to form hydrogels in the interstices of the ePTFE material was achieved by exposing each side of the disk (luminal and abluminal) to long-wave ultraviolet radiation for 5 minutes as in the previous examples. The disks were soaked in phosphate-buffered saline solution for one hour prior to implantation.

Impregnated and control ePTFE disks were randomly implanted both subcutaneously and within epididymal fat of sprague-dowley rats (n=3 per treatment per tissue), according to the techniques discussed in Boswell, et al., Denucleation Promotes Neovascularization Of ePTFE In Vivo, J. Biomater. Sci. Polym. Ed., 10(3):319–29 (1999). Rats were anesthetized and prepped for surgery. A pentobarbital sodium injection into the peritoneal cavity was used to anesthetize the animals (Nembutal® sodium solution, 15 mg per kg of rat). Two small incisions over the right and left haunch were made, and the dermis was separated from the subdermis at both sites to allow insertion of randomly selected samples. Following sample insertions, wounds were closed with tissue clips. Another incision was made through the lower abdominal wall into the peritoneal cavity. The testicles were pushed gently in from the outside to force the epididymal fat into the surgical field. Sample were placed in folds of each fat pad and sutured in two places. Closure was done with absorbable sutures along the linea alba followed by sutures in the skin. Animals were allowed to recover. At four weeks post-implantation, the implants were retrieved for histological analyses while the animal was anesthetized. Retrieved disks are stored in a fixative, and the rats were euthanized.

The fixed impregnated ePTFE disks were prepared for histological assessment. Paraffin blocks were made using standard histology techniques. Particular care is given to the position of the disks in the paraffin block in a manner that allows for cutting in a direction parallel to the graft fibrils. The histological slides were prepared, and stained with hematoxylin and eosin (H&E) and with Griffonia simplicifolia-1 immunostain (GS1), a peroxidase stain that allows for the visualization of microvessels by binding to antigens found in endothelial cells. To quantify the vascular profile in and around the ePTFE implants, histological slides were observed with an inverted optical microscope using a 40× objective accompanied with a grid. The tetramethylrhodamine labels aided in visualizing the gel within the implant under epifluorescence microscopy. The number of microvessels present on a 2916 $\mu m^2$ area (n=5 per slide) at the abluminal interface was averaged in two groups: vessels inside the implants (neovascularization) and vessels in the surrounding tissue (angiogenesis). These numbers were expressed as density of blood vessel (number of microvessels per $mm^2$), and statistical comparisons between the control group and the treatment were made. A bar graph showing the microvessel count for the ePTFE disks is found in FIG. 1.

Figure 2A:
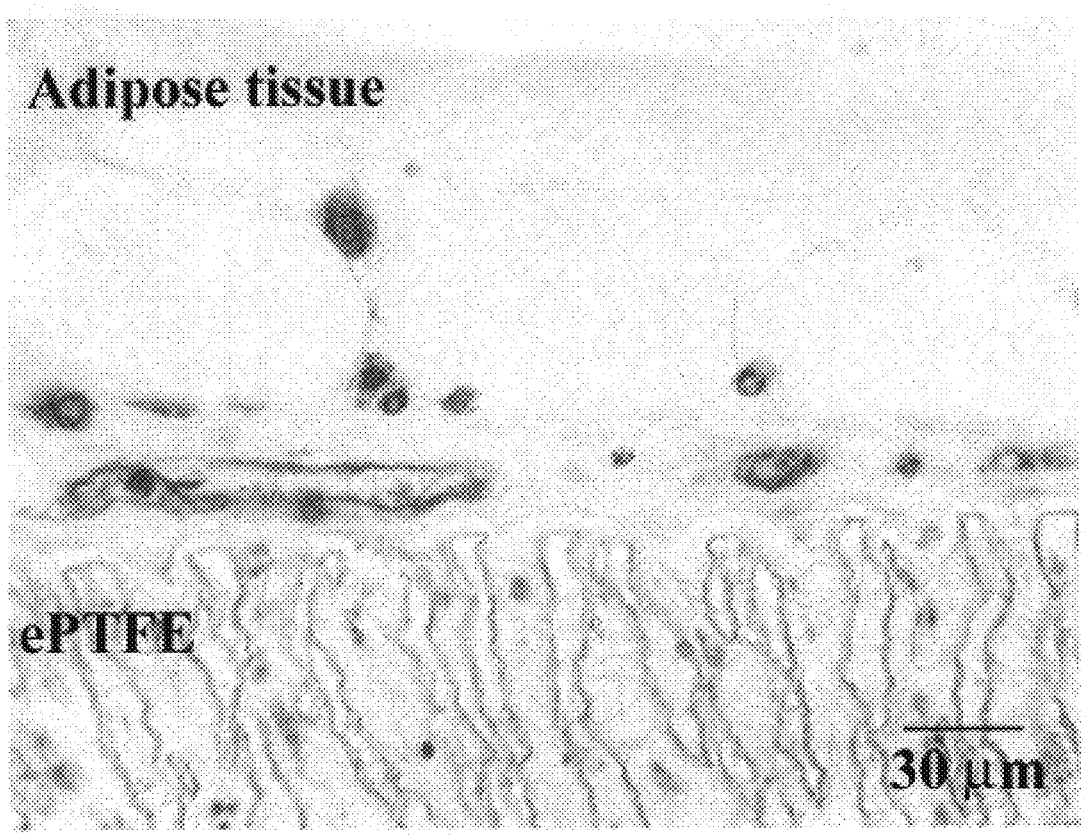
FIGS. 2A and 2B are light micrographs of the abluminal interface of a control and impregnated ePTFE disk, respectively, implanted in the adipose tissue of rats.
Figure 2B:
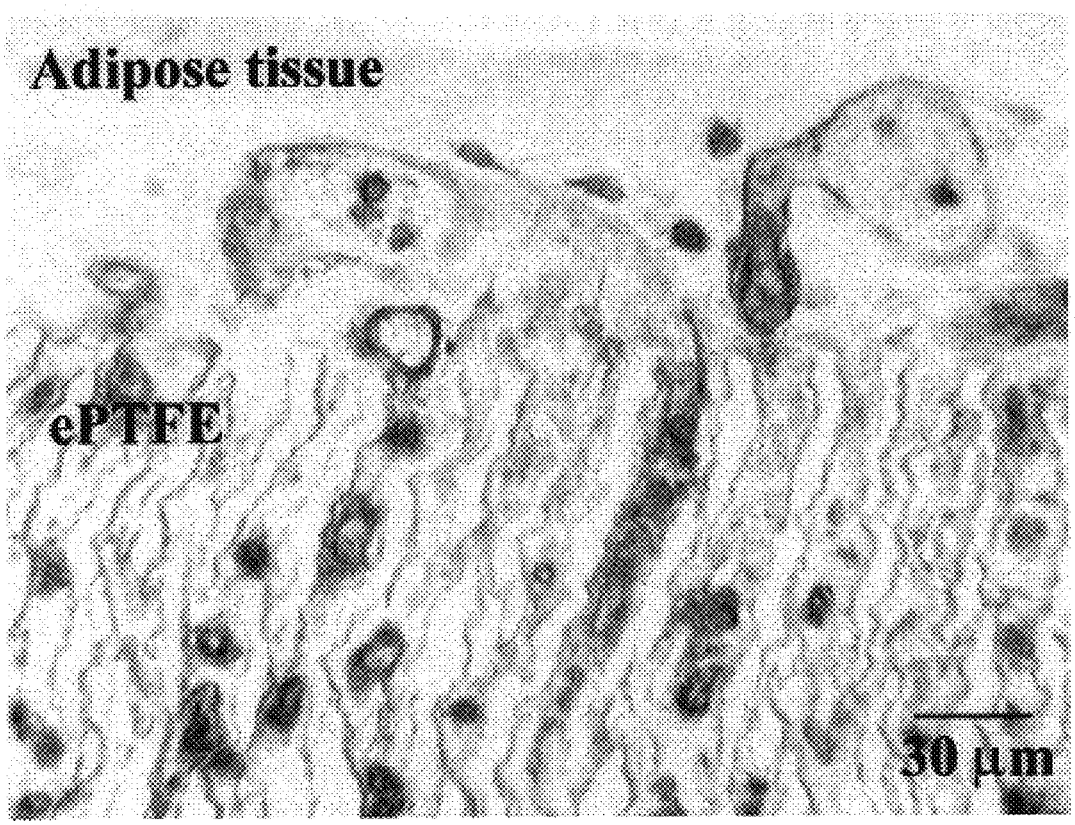

As can be seen from FIG. 1, the inventive hydrogels exhibited an improvement in angiogenesis and neovascularization. The comparative implants (i.e., the unimpregnated control implant, the dextran impregnated implant, and the HyA impregnated implant) all exhibited angiogenesis and neovascularization counts of less than 1000 and 500 microvessels, respectively. To the contrary, the implant impregnated with the 0.4% Dex-HyA hydrogel exhibited a neovascularization count of about 1000 which is more than double the counts of the comparative implants. A further improvement in both angiogenesis and neovascularization counts were observed for the implant impregnated with the 4% Dex-HyA hydrogel, which exhibited counts of about 1500 and 1250, respectively. In addition, FIGS. 2A and 2B, which are light micrographs of the abluminal interface of the control and 4% Dex-HyA implants in the adipose tissue, show red blood cells in the newly formed blood vessels of the impregnated implant indicating the establishment physiologic functions. Thus, the inventive hydrogels provide angiogenic and vascularizing activity with the use of non-angiogenic hyaluronate.

It will be apparent to those skilled in the art that various modifications and variations can be made without departing from the spirit or scope of the invention. Thus, it is intended that the present invention cover the modifications and variations of this invention, provided they come within the scope of the appended claims and their equivalents.

We claim:

1. A hydrogel having angiogenic and vascularizing activity prepared by a process which comprises:

admixing a polysaccharide material at least partially substituted with an unsaturated, cross-linking moiety, and a non-angiogenic hyaluronic acid or a salt thereof, with a free-radical initiator in a solvent; and cross-linking the mixture to form the hydrogel having angiogenic and vascularizing activity.

2. The hydrogel of claim 1, wherein the free-radical initiator is selected from the group consisting of chemical initiators and non-chemical initiators.

3. The hydrogel of claim 2, wherein the non-chemical initiator is an ultraviolet initiator.

4. The hydrogel of claim 3, wherein the ultraviolet initiator is an acetophenone derivative.

5. The hydrogel of claim 1, wherein the polysaccharide material has an average molecular weight of at least about 10,000 Daltons.

6. The hydrogel of claim 5, wherein the average molecular weight of the polysaccharide material is at least about 40,000 Daltons.

7. The hydrogel of claim 1, wherein the polysaccharide material is selected from the group consisting of a starch or starch derivative, a water-soluble gum, and mixtures thereof.

8. The hydrogel of claim 1, wherein the water-soluble gum is selected from the group consisting of alginates, carrageenans, xanthans, galactomannans, and mixtures thereof.

9. The hydrogel of claim 1, wherein the starch or starch derivative is dextran.

10. The hydrogel of claim 1, wherein the unsaturated, cross-linking moiety is selected from the group consisting of esters, ethers, thioethers, amides, enamides, sulfonyl esters, and mixtures thereof.

11. The hydrogel of claim 1, wherein the unsaturated, cross-linking moiety is an acrylate group.

12. The hydrogel of claim 1, wherein the non-angiogenic hyaluronic acid or salt thereof has an average molecular weight of at least about 500,000 Daltons.

13. The hydrogel of claim 12, wherein the average molecular weight of hyaluronic acid or salt thereof is at least about 1,000,000 Daltons.

14. The hydrogel of claim 1, wherein the solvent is selected from the group consisting of water, water-based solvents, water-miscible organic solvents and mixtures thereof.

* * * * *